United States Patent
Guthery

(10) Patent No.: US 8,420,627 B2
(45) Date of Patent: Apr. 16, 2013

(54) NASAL, WOUND AND SKIN FORMULATIONS AND METHODS FOR CONTROL OF ANTIBIOTIC-RESISTANT STAPHYLOCOCCI AND OTHER GRAM-POSITIVE BACTERIA

(76) Inventor: B. Eugene Guthery, Texarkana, TX (US)

( * ) Notice: Subject to any disclaimer, the term of this patent is extended or adjusted under 35 U.S.C. 154(b) by 0 days.

(21) Appl. No.: 13/496,184

(22) PCT Filed: Sep. 17, 2010

(86) PCT No.: PCT/US2010/049336
§ 371 (c)(1),
(2), (4) Date: Mar. 14, 2012

(87) PCT Pub. No.: WO2011/035158
PCT Pub. Date: Mar. 24, 2011

(65) Prior Publication Data
US 2012/0178731 A1 Jul. 12, 2012

Related U.S. Application Data

(60) Provisional application No. 61/257,922, filed on Nov. 4, 2009, provisional application No. 61/243,455, filed on Sep. 17, 2009.

(51) Int. Cl.
*A61K 31/555* (2006.01)
*A61K 31/23* (2006.01)
*A61K 31/045* (2006.01)

(52) U.S. Cl.
USPC ............................ 514/188; 514/552; 514/724

(58) Field of Classification Search .................. 514/188, 514/552, 725
See application file for complete search history.

(56) References Cited

U.S. PATENT DOCUMENTS

| | | | |
|---|---|---|---|
| 5,602,183 | A | 2/1997 | Martin et al. |
| 5,776,919 | A | 7/1998 | Sukigara et al. |
| 5,840,760 | A | 11/1998 | Carraher, Jr. et al. |
| 6,156,792 | A | 12/2000 | Hatton et al. |
| 6,395,746 | B1 | 5/2002 | Cagle et al. |
| 6,461,624 | B2 | 10/2002 | Eggers et al. |
| 7,014,850 | B2 | 3/2006 | Fischetti et al. |
| 2002/0048592 | A1 | 4/2002 | Eggers et al. |
| 2003/0211995 | A1 | 11/2003 | Kokai-Kun et al. |
| 2003/0224000 | A1 | 12/2003 | Kokai-Kun et al. |
| 2004/0266886 | A1 | 12/2004 | Seipel et al. |
| 2005/0089539 | A1 | 4/2005 | Scholz et al. |
| 2006/0051384 | A1 | 3/2006 | Scholz et al. |
| 2006/0051385 | A1 | 3/2006 | Scholz et al. |
| 2006/0052452 | A1 | 3/2006 | Scholz et al. |
| 2007/0241306 | A1 | 10/2007 | Wehner et al. |
| 2007/0286813 | A1 | 12/2007 | Toutounghi |
| 2008/0267890 | A1 | 10/2008 | Palermo et al. |

OTHER PUBLICATIONS

Barclay, L., "Mupirocin Resistance May Be Common in MRSA Clinical Isolates," National Foundation for Infectious Disease (NFID) 2008 Annual Conference on Antimicrobial Resistance, p. 1-2 (2008).
Chirife, J., et al., "In Vitro Antibacterial Activity of Concentrated Polyethylene Glycol 400 Solutions," Antimicrob Agents & Chemo, vol. 24 (3): 409-412 (1983).
Cookson, B., "The Emergence of mupirocin resistance: a challenge to infection control and antibiotic prescribing practice," J Antimicrob Chemo, vol. 41: 11-18, (1998).
Hedin, G. and Fang, H., "Evaluation of Two New Chromogenic Media, CHROMagar MRSA and *S. aureus ID*, for Identifying *Staphylococcus aureus* and Screening Methicillin Resistant *S. aureus*," J Clin Microbiol, vol. 43 (8) : 4242-4244, (Aug. 2005).
Kabara, J. J., et al., "Fatty acids and Derivatives as Antimicrobial Agents," Antimicrobial Agents & Chemo, vol. 2 (1): 23-18, (1972).
Kabara, J.J., et al., "Antimicrobial Lipids: Natural and Synthetic Fatty Acids and Monoglycerides," Lipids, vol. 12 (9): 753-759, (1977).
Kelsey, J.A., et al., "Fatty Acids and Monoacylglycerols Inhibit Growth of *Staphylococcus aureus*," Lipids, vol. 41 (10):951-961, (2006).
Kubo, I., et al., "Structural Functions of Antimicrobial Long-chain Alcohols and Phenols," Bioorganic & Medicinal Chem, vol. 3 (7): 873-880 (1995).
McColligan, C., "Got MRSA?" [Publication date unknown; latest publication date on articles referenced—2005].
McDonald, M. I., et al., "Antibacterial Activity of Hydrolyzed Linseed Oil and Linolenic Acid against Methicillin-Resistant *Staphylococcus aureus*," Lancet, p. 1056, Nov. 7, 1981.
Mupirocin Official FDA information, side effects and uses, Professional Information; http://www.drugs.com/pro/mupirocin-ointment.html, p. 2-5, (Jun. 23, 2009).
Nair, M., et al., "Antimicrobial Effect of Caprylic Acid and Monocaprylin on Major Bacterial Mastitis Pathogens," J Dairy Sci, vol. 88:3488-3495 (2005).
Rouse, M., et al., "In Vitro and In Vivo Evaluations of the Activities of Lauric Acid Monoester Formulations against *Staphylococcus aureus*," Antimicrobial Agents and Chemotherapy, vol. 49 (8): 3187-3191, (2005).
Togashi, N., et al., "Antibacterial Activity of Long-Chain Fatty Alcohols against *Staphylococcus aureus*," Molecules, vol. 12: 139-148 (2007).
Von Eiff, C., et al., "Nasal Carriage as a Source of *Staphylococcus aureus* Bacteremia," New Engl J Med, vol. 344 (1): 11-16 (2001).
Von Eiff, C., et al., "Nasal Carriage as a Source of *Staphylococcus aureus* Bacteremia," New Engl J Med, vol. 344 (1): 11-16, (2001).
Woolford, M., "Microbiological Screening of the Straight Chain Fatty Acids (C1-C12) as Potential Silage Additives," J Sci Fd Agric, vol. 26:219-228, (1975).

*Primary Examiner* — Raymond Henley, III
(74) *Attorney, Agent, or Firm* — Hemingway & Hansen, LLP; D. Scott Hemingway

(57) ABSTRACT

Formulations and methods are disclosed which are effective to kill or control bacteria in the nares including gram-positive bacteria strains of *S. aureus* that are antibiotic resistant (MRSA—methicillin-resistant *Staphylococcus aureus*. A preferred composition comprises one or more medium-chain alcohols (dodecanol), glycerol monoesters (glycerol monocaprylate or glycerol monolaurate), and/or benzoic acid or benzoic acid analog, in a suitable pharmaceutical carrier, preferably an ointment, along with an odorant compound, preferably eucalyptus oil. The formulations and variations of the formulation may also be used on open wounds or lesions as well as intact skin.

27 Claims, No Drawings

NASAL, WOUND AND SKIN FORMULATIONS AND METHODS FOR CONTROL OF ANTIBIOTIC-RESISTANT STAPHYLOCOCCI AND OTHER GRAM-POSITIVE BACTERIA

CROSS REFERENCE TO RELATED APPLICATIONS

This application claims the benefit of U.S. Provisional Application 61/243,455 filed 17 Sep. 2009 and U.S. Provisional Application 61/257,922, filed 4 Nov. 2009.

TECHNICAL FIELD

This invention relates to the field of treating humans colonized or infected with antibiotic-resistant gram-positive bacteria.

BACKGROUND OF THE INVENTION

Antimicrobial resistance occurs when bacteria change or adapt in a way that allows them to survive in the presence of antibiotics designed to kill them. In some cases bacteria become so resistant that no available antibiotics are effective against them, and such resistance limits or even eliminates the therapeutic options. Gram-positive bacteria such as *Staphylococcus aureus* and *Enterococcus faecalis* are particularly problematic because they can cause a range of diseases including skin lesions, bacteremia, sepsis, pneumonia, endocarditis and osteomyelitis. Skin lesions can easily progress to life-threatening blood or bone infections. Some strains of antibiotic-resistant *S. aureus* also produce the destructive Panton-Valentine leukocidin toxin.

One of the bacteria discussed above, *Staphylococcus aureus* has long been recognized as particularly problematic as a pathogen in human diseases. Staphylococcal infections occur regularly in hospitalized patients. In recent years, an increasing number of these infections are caused by Methicillin-resistant *Staphylococcus aureus* (MRSA) strains, which are most often resistant to multiple antibiotics. MRSA has become a major nosocomial pathogen in many hospitals worldwide and has also become a leading cause of colonization and infection in both acute and chronic soft-tissue wounds. MRSA also is increasingly an active pathogen outside the hospital setting.

Three types of MRSA are currently recognized:
- HA-MRSA—(HA—hospital acquired) Methicillin resistant *Staphylococcus* acquired in hospitals or healthcare facilities, including in such facilities as nursing homes and dialysis centers
- CA-MRSA—(CA—community acquired) Methicillin resistant *Staphylococcus* acquired in a community setting,
- USA 300—A community acquired strain which is not only resistant to Methicillin, but is also resistant to Vancomycin. This strain is found most prevalently in schools, prisons, among athletic teams, and within the homosexual community.

Frequently wounds and skin lesions become infected with MRSA by transfer of organisms from the nasal passages to the wound via the hands. Wounds may also become infected by the introduction of MRSA from community-acquired MRSA sources. This may occur when an individual has the skin colonized with the CA-MRSA strain or USA-300 strain if the skin integrity is broken through minor trauma or from vascular insufficiency due to, for example, diabetes.

It is important to note that all three types of MRSA can be spread by human to human contact, or animal to human contact, and may exhibit different epidemiology.

The difference between MRSA and methicillin-susceptible *S. aureus* (MSSA) is resistance to β-lactamase-stable β-lactam antibiotics. MRSA strains that are resistant to β-lactam antibiotics and other antibiotics have generally maintained a high level of in vitro susceptibility to vancomycin, although slight changes with in vitro activity could vastly change clinical activity. As a result, vancomycin has become the mainstay of therapy for invasive infections due to MRSA strains. Unfortunately, clinical strains of *S. aureus* with intermediate resistance to vancomycin were reported in 1996, followed in 2002 with reports of isolates that were fully resistant. As use of vancomycin increases, the probability of resistance increases as well. Over-prescribing of antibiotics is recognized as a key factor in the development of resistance. The Center for Disease Control has even begun a campaign to prevent antimicrobial resistance which teaches the judicious use of antimicrobials while particularly avoiding the overuse of broad-spectrum antibiotics with the hope of stemming the increased prevalence of antibiotic resistance.

One of the most prevalent ecological niches of *S. aureus* strains and other gram-positive pathogenic bacteria is the anterior nares. Epidemiology indicates that organisms often spread from the nose to other parts of the body through human behavior. For example, children often wipe their noses with their hands, thereby transforming hands into a vehicle for spreading disease to other parts of the body and to other humans. Even adults may unconsciously spread organisms in this way. Some attempts have been made to address MRSA and other gram-positive organisms in the nares via a treatment agent. An example of such an agent is mupirocin (Bactroban, Glaxo-SmithKline, Beacham Pharmaceuticals, Philadelphia, Pa.). This antibiotic has been reported to have some efficacy against nasal MRSA when used as recommended, but the efficacy is dependent upon the susceptibility or resistance of the particular strain of MRSA to mupirocin. The recommendation is that the agent be used for short courses (application to the anterior nares twice daily for five days). The preparation is provided as 2% mupirocin calcium in a cream or ointment base for nasal application. It should be noted that mupirocin has not been approved for use in children under the age of 12.

However, mupirocin therapy has led to the development of antibiotic resistance in patients. In some cases, the development of resistance has been rapid and the resistance may become problematic, especially when the product is used prophylactically. See B. D. Cookson, "The emergence of mupirocin resistance: a challenge to infection control and antibiotic prescribing practice," *Journal of Antimicrobial Chemotherapy* (1998) 41, 11-18.

There is a continuing need for novel, safe and effective treatment compositions which will eliminate or reduce carriage of gram-positive pathogens in nares, wounds, and other loci of colonization on the human body.

DETAILED DESCRIPTION OF THE INVENTION

Nasal, skin and wound formulations for the eradication or substantial reduction of gram-positive organisms are now disclosed.

In a preferred embodiment for topical application to the skin and wounds, the formulation comprises a synergistic mixture of: one or more aliphatic alcohols having nine to twelve carbons, most preferably dodecanol; a fatty acid glycerol ester, most preferably selected from the group consisting of glycerol monolaurate, glycerol monocapric acid, glycerol monocaprylate and mixtures thereof, and an organic acid, preferably selected from the group consisting of benzoic acid or benzoic acid analogs, lactic acid, mandelic acid or malic acid, and acetic acid, most preferably benzoic acid or a benzoic acid analog.

In an alternative formulation for application to skin, wounds and/or the anterior nares, the formulation comprises a combination of an aliphatic alcohol having nine to twelve carbons, most preferably dodecanol, in an amount of 10% or less of said formulation, and a fatty acid glycerol ester, most preferably selected from the group consisting of glycerol monolaurate, glycerol monocapric acid, glycerol monocaprylate, and mixtures thereof.

The preferred C9-C12 aliphatic alcohol ingredient of the formulation has been reported as having activity against bacteria in vitro. However, these alcohols have not been employed in a method for eradicating MRSA bacteria on skin. In particular, there has been no known teaching of application to open wounds, or the anterior nares. Although such alcohols have been listed as toxic or otherwise dangerous when applied to the human body at some concentrations, dodecanol has been used at very low concentrations as an emollient in cosmetic preparations. It has now been found that when used in combination with the other components of the novel formulation, the concentration of dodecanol can be lowered below the amount heretofore thought to be irritating, while still maintaining efficacy of the formulation against MRSA bacteria.

It has been found that a low concentration of C9-C12 aliphatic alcohol in combination with a fatty acid glycerol ester is effective in eliminating or greatly reducing the concentration of MRSA S. aureus upon topical application to an area of the human body in which said bacteria is residing. Increased efficacy is achieved by pairing said aliphatic alcohol with a fatty acid glycerol ester, most preferably selected from the group consisting of glycerol monolaurate, glycerol monocapric acid, glycerol monocaprylate and mixtures thereof. The concentration of C9-C12 aliphatic alcohol is from about 25 micrograms/mL to about 0.05 grams/mL. The concentration of said fatty acid glycerol ester is from about 20 micrograms/mL to about 0.05 grams/mL.

Another embodiment of the invention is a method for treating the nares with a formulation capable of achieving a greater than seven or greater than eight log kill of gram-positive bacteria in vitro in one minute or less. In this method, the formulation comprises a C9-C12 aliphatic alcohol in a concentration from about 100 micrograms/mL to about 0.05 grams/mL and a fatty acid glycerol ester in a concentration from about 125 micrograms/mL to about 0.05 grams/mL.

In a preferred embodiment, a method for treating nares, skin or wounds with a formulation comprising a C9-C12 aliphatic alcohol, a fatty acid glycerol ester and an organic acid which together provide a synergistic effect is disclosed. The concentration of each component can be lowered as compared with the two-component formulation of the invention due to this synergism. Each component can be lowered to a concentration that is one-fourth or less of the component's individual MIC and still remains effective at eradicating the MRSA organisms. Effective ranges for the components are: dodecanol 20 micrograms to 5.0 grams; glycerol monolaurate 15 micrograms to 5.0 grams; and benzoic acid 250 micrograms to 4.0 grams per 100 grams of ointment base. A preferred amount of benzoic acid is about 2 grams per 100 grams of ointment base.

In another embodiment, additional components may be added to the formulation when it is intended for the treatment of wounds or catheter sites. Components, such as phenyl ethyl alcohol and acetic acid, which are known in the art to inhibit the growth of gram-negative bacteria, may be included. Components, such as acetic acid or zinc pyrithione, which help to prevent colonization by yeasts and molds, may also be included in preparations intended to be used on catheter sites. A preferred amount of acetic acid is 3%. A preferred amount of zinc pyrithione is 0.25%.

In yet another embodiment, the formulation may be used as an adjuvant to existing over-the-counter (OTC) antibiotic preparations such as those containing neomycin, Polymyxin B and Bacitracin, or their combinations. For example, the formulation of the invention can be added to Bacitracin intended for application to the anterior nares and the ability of the combined agents to eradicate MRSA will be greatly increased.

The formulation as an adjuvant may also be added to antiseptic preparations and alcohol gels containing short-chain aliphatic alcohols in concentrations greater than fifty percent by volume. In this application, the formulation provides an antibacterial enhancing agent for these preparations, increasing the effectiveness of treatment to include gram-positive bacteria, as well as MRSA.

Formulation of Novel Ointment for MRSA Eradication in the Nares

A preferred formulation comprises an aliphatic alcohol such as dodecanol, a fatty acid glycerol ester such as glycerol monolaurate, and a benzoic acid analog such as benzoic acid, along with a carrier base which adapts to mucus membrane adherence.

A representative formulation is exemplified below.

Example Formula I

| Ingredient | Amount/100 grams | Function |
|---|---|---|
| Petrolatum | 55.0 grams | Carrier base and emollient |
| Propylene glycol | 10.0 grams | Carrier base and emollient |
| Polawax | 15.0 grams | Emulsifier |
| Dodecanol | 5.0 cc | Antimicrobial and penetrating agent |
| Glycerol monolaurate | 5.0 grams | Antimicrobial and emollient |
| Benzoic acid | 2.0 grams | Antimicrobial |
| Eucalyptus oil | 2.0 cc | Odorant |
| Water, DI | 6.0 grams | Diluent |

To prepare the novel ointment of this invention, petrolatum and Polawax are heated slowly to melt the products. Proylene glycol is added to the liquified petrolatum and Polawax with stirring to produce a homogenous mixture. The medium-chain alcohol(s), fatty acid ester(s), benzoic acid, eucalyptus oil and water are added and stirred to produce a homogenous mixture. While slowly stirring, the solution is allowed to return to room temperature.

An alternative representative formulation is exemplified below.

Example Formula II

| Ingredient | Amount/100 grams | Function |
|---|---|---|
| PEG 400 | 80 grams | Carrier base and emollient |
| PEG 3350 | 12.5 grams | Carrier base and emollient |
| Dodecanol | 4.0 grams | Antimicrobial and penetrating agent |
| Glycerol monolaurate | 3.0 grams | Antimicrobial and emollient |
| Benzoic acid | 0.50 grams | Antimicrobial |

To prepare the alternative formulation of the novel ointment of this invention, PEG 3350 is heated slowly to melt the product. The PEG 400 is added to the PEG 3350 and stirred to produce a homogenous solution. The medium-chain alcohol(s), fatty acid ester(s) and benzoic acid are added and stirred to produce a homogenous solution. While slowly stirring, the solution is allowed to return to room temperature.

The aliphatic alcohol of the formulation is selected so that it can be employed at a concentration and pH compatible with contact with the mucous membranes or open wounds. The appropriate pH of the product will depend upon the application site. The pH may be lowered to 4.0 for products applied to the squamous epithelium that covers the distal nares (vestibule). For wounds, it is preferable to keep the pH as near to 7.4 as possible.

The composition comprises an aliphatic alcohol, preferably C9-C12, preferably C10-C12, and most preferably C12. Aliphatic alcohols C10-C12 have been found to be effective at inhibiting common strains of staphylococci, but not MRSA, at ranges of 12.5-50 micrograms/mL. Dodecanol (C12) specifically has been found to be effective against Methicillin resistant S. aureus (MRSA), Vancomycin intermediate S. aureus (VISA) and Vancomycin resistant Enterococcus faecalis (VRE) at 83 micrograms/mL. See Table II below.

The formulation further comprises a fatty acid glycerol ester. The fatty acid glycerol ester is selected from a group of 010-013 glycerol esters. The fatty acid glycerol ester is preferably a glycerol monoester, preferably selected from the group consisting of glycerol monolaurate, glycerol monocaprin and glycerol monocaprylate. Most preferably, the glycerol monoester is glycerol monolaurate.

The formulation further comprises an organic acid. The organic acid is selected to be non-irritating to human tissues at the concentration employed. The pH should be near 7.4 if applied to a wound. Mineral acids, such as hydrochloric acid and sulfuric acid, should be avoided. Acids of choice would be selected from among benzoic acid and benzoic acid analogs, lactic acid, mandelic acid, and malic acid. Most preferably, benzoic acid is employed as the organic acid component.

The combination of an aliphatic alcohol, fatty acid ester, and organic acid provides a formulation having antibacterial activity that far exceeds the antibacterial activity of any component employed alone, and it is demonstrated here that a synergistic relationship exists between the three components. A combination using each of the components at less than 25% of the individual MIC concentrations was as effective against S. aureus MRSA as the individual components at full concentration.

The formulation preferably further comprises a penetrating agent. Use of a penetrating agent is preferred so that the formulation may penetrate through dry crusty material which may be found inside the nasal cavity, thus permitting the antimicrobials better contact with the affected nasal tissues and mucous membranes. The penetrating abilities would also benefit in the treatment of wounds, which may also be covered with crusty material or scabs, allowing the formulation to reach the deeper layers of the wound which may be colonized with MRSA.

It has been found that the aliphatic alcohol dodecanol not only can be used as one of the synergistic components of the formulation, but that it has dual activity as a penetrating agent. The inclusion of an additional preferred penetrating agent, such as lecithin phosphate at concentrations up to 20% (available from HUMCO, Texarkana, Tex.), may be advantageous when the formulation will be used on wounds. Isopropyl myristate, at a concentration of 2%, is another preferred penetrating agent which may be used. Many other permeation enhancers are known in the art which could also be used in the formulation, including polar solvents, and amphiphilic compounds containing a polar head and a hydrophobic chain.

The formulation preferably further comprises one or more components which provide an ointment base for the formulation. Care must be taken to select base components which are compatible with the active ingredients of the formulation for the particular application. It has been found that some common ointment base components may inhibit one or more of the active ingredients of the formulation causing a decrease in the desired bactericidal activity. Polyethylene glycols (PEG) are among the ointment bases which may cause inhibition of bactericidal activity of the formulation, possibly by causing bacterial cells to clump, and therefore such components should be avoided. Preferred ointment bases are petrolatum, propylene glycol, Polawax, and combination thereof. Petrolatum and propylene glycol also have secondary uses as emollient agents in ointment preparations. There may be specific applications wherein PEG containing formulations are advantageous, but for the nasal formulation, the use of petrolatum, propylene glycol and Polawax in the ointment base is most preferred.

The formulation further comprises odorant compounds such as eucalyptus oil. In addition to being a useful odorant for nasal applications, eucalyptus oil is known to have antibacterial properties. Other odorant compounds such as thymol and spearmint may be added to certain embodiments of the formulation to increase aesthetic appeal to the user.

The concentration of the ingredients may be higher when used on intact skin or the anterior nares. The concentration should be high enough in the anterior nares to achieve a seven to eight log kill within one minute.

For use in wounds a formulation comprising lower concentrations of the components may be used. Components of the formulation would be metabolized following application to a wound leading to a decrease in the amount of the formulation remaining in the wound; however, the combination of the components would have a residual bacteriostatic effect in the wound thereby preventing recontamination.

The formulation of the invention is adapted for application inside the human nares in a method of treatment to reduce or eliminate S. aureus and/or other gram-positive pathogenic bacteria. The perianal area is also a prevalent site for MRSA colonization and this area could be treated with the formulation ointment concurrently with treatment of the nares to insure complete eradication of MRSA from both the nose and perianal areas of the patient.

In one method, the formulation is applied to the anterior nares. One application of the formulation effectively eradicates all or nearly all of the gram-positive bacteria within one minute of contact.

In another method of use, the treatment regimen includes multiple applications to ensure eradication. One regimen comprises the application of the formulation to the anterior nares every twelve hours for three to five consecutive days.

The formulation may also be applied to the skin, or to wounds and lesions located elsewhere on the body which may be infected with gram-positive bacteria. For example, there are multiple dermatoses which produce a disruption in skin integrity, in which gram positive bacteria reside. A regimen comprises application of the preparation to the wound or lesion site every twelve hours until the infection has been eradicated.

In another embodiment, the active ingredients of the formulation, dodecanol, glycerol monolaurate, benzoic acid and eucalyptus oil, may be used in combination with other topical antiseptics to produce a hand and body wash useful for the eradication of MRSA from those body surfaces not treated with the ointment formulation. Such a hand and body wash could be used as an adjunct therapy to treatment of the nares and perianal regions in a whole body MRSA eradication regimen.

In addition to the active ingredients of the formulation, dodecanol, glycerol monolaurate, benzoic acid and eucalyptus oil, components that help to prevent colonization by yeasts and molds, such as acetic acid or zinc pyrithione, may also be included in hand and body wash preparations. A preferred amount of acetic acid is 3%. A preferred amount of zinc pyrithione is 0.25%.

A representative formulation for use as an alcohol-based hand and body wash is described below.

Example Formulation III

| Ingredient | Amount/100 grams | Function |
| --- | --- | --- |
| Ethyl alcohol | 68.42 cc | Antimicrobial |
| Emery 315 | 4.00 cc | Surfactant/conditioner |
| Almond Oil | 4.00 cc | Emollient |
| Medium chain triglycerides | 3.00 cc | Emollient |
| Dodecanol | 2.50 cc | Antibacterial/penetrating agent |
| Glycerol monolaurate | 2.50 grams | Antimicrobial/emollient |
| Eucalyptus globules | 2.00 cc | Odorant |
| Benzoic acid | 2.00 grams | Antimicrobial |
| Glycerin | 2.00 cc | Humectant/protectant |
| Lactic acid | 2.00 cc | Humectant/conditioner |
| Vitamin E | 2.00 cc | Antioxidant |
| Spearmint | 1.00 cc | Odorant |
| Klucel | 1.00 cc | Emulsion stabilizer |
| Thymol | 0.50 grams | Odorant |
| DI Water | 3.08 cc (Q.S. to 100 cc) | Diluent |

One advantage of the formulation is that it is not subject to the restrictions of antibiotic use previously discussed. The formulations disclosed do not present a high risk of creating strains with antimicrobial resistance, unlike antibiotics, said antibiotics being naturally or synthetically derived from microbial sources. One of the characteristics of the formulation is that it comprises multiple antimicrobial components thus reducing the possibility that resistance to any one component may occur. Another characteristic of the disclosed formulation is the synergistic effect that occurs when all three components, dodecanol, glycerol monolaurate and benzoic acid, are used together thus allowing for a smaller effective amount of each component to be employed.

Ingredients to enhance the aesthetic qualities of the nasal ointment may be included into the formulation. These ingredients may include odorants or additional emollients. While eucalyptus oil is the preferred odorant for the formulation, odorants in addition to eucalyptus oil may be employed. A preferred ingredient is 0.2% eucalyptus oil.

Use of Aliphatic Alcohols in Formulation

Straight and branched-chain alcohols C9-12 are preferred. The more preferred are straight-chain alcohols from C10-12. See Table I below. The most preferred straight chain alcohol is dodecanol (lauryl alcohol or 1-dodecanol). See Kubo, et al. "Structural Functions of Antimicrobial Long-chain Alcohols and Phenols." *Bioorganic & Medicinal Chemistry* (1995) Vol. 3 No. 7, pp. 973-880.

TABLE I

Effective Bactericidal Concentration of Primary Alcohols against *Staphylococcus* (in Micrograms/mL)

| C-8 | C-9 | C-10 | C-11 | C-12 | C-13 |
| --- | --- | --- | --- | --- | --- |
| 800 | 200 | 50 | 25 | 12.5 | >800 |

Now reported are in vitro Minimum Inhibitory Concentrations (MIC) for dodecanol against *Staphylococcus aureus* MRSA, ATCC 33591, *Staphylococcus aureus* VISA (Vancomycin intermediate sensitivity) ATCC 700699, and *Enterococcus faecalis* ATCC 51299 (formerly *Streptococcus faecalis* VREF (vancomycin resistant)). One tenth of a cc of dodecanol was diluted with 50 cc of polyethylene glycol 400 and 449.9 cc of sterilized deionized water, followed by five doubling dilutions. The results are shown in Table II. The MIC for dodecanol against the antibiotic-resistant strains tested is 83 µg/mL. When combined with the other components of the formulation, a synergistic effect is seen such that bactericidal activity is still maintained even when the concentration of dodecanol is reduced to 20 µg/mL.

TABLE II

Test Results for Dodecanol
Final Concentration (µg/mL)

| Challenge Organism | 83 | 41.5 | 20.25 | 10.125 | 5.0625 | 2.53125 | MIC |
| --- | --- | --- | --- | --- | --- | --- | --- |
| S. aureus MRSA | 0 | + | + | + | + | + | 83 |
| S. aureus VISA | 0 | + | + | + | + | + | 83 |
| E. faecalis VRE | 0 | + | + | + | + | + | 83 |

Results expressed as Growth (+) or No Growth (0)
MIC = Minimum Inhibitory Concentration The example formulation above includes C12 (dodecanol). The specific gravity of dodecanol is 0.83. Therefore, one cc weighs 0.83 grams or 830,000 micrograms. One cc in ten liters is still 83 micrograms/mL. At these low concentrations dodecanol has no irritating effects on the mucous membranes.

As discussed above, dodecanol is also an effective permeation enhancing agent promoting penetration into the affected tissues while being physiologically acceptable for contact with said tissues at the concentrations employed in the formulation herein.

The preferred concentration of dodecanol is 0.0000001 percent to 5.0 percent. A more preferred concentration is 0.0001 to 2.5 percent. The most preferred concentration of dodecanol is 0.1 to 1.0 percent by volume.

Use of Glycerol Esters of Fatty Acids in Formulation

Fatty acids and their glycerol esters have been shown to exhibit antimicrobial activity against a wide range of organisms, including gram-positive bacteria. In addition, not only are these glycerol esters of fatty acids not irritating to mucous membranes, they provide an emollient effect on the treated tissue.

Several glycerol esters of fatty acids are available. Monocaprin (glycerol monocaprylate) is a ten carbon fatty acid ester. Monolaurate (glycerol monolaurate) is a twelve carbon fatty acid ester. Dilaurin is the two carbon glycerol ester of lauric acid. Tridecanoyl monoglyceride is the thirteen carbon fatty acid ester. These fatty acid glycerol esters were tested in vitro for activity against S. aureus to determine the Minimum Inhibitory Concentrations (MIC) in micrograms/mL. The minimum inhibitory concentrations in micrograms/mL of these glycerol esters of fatty acids were tested in vitro for their activity against S. aureus. The ten and twelve carbon forms have been proven to be effective against MRSA. The results are in Table III. See Kabara, et al. "Antimicrobial Lipids: Natural and Synthetic Fatty Acids and Monoglycerides." Lipids (1977) Vol. 12 (9), pp. 753-759.

TABLE III

Glycerol Esters of Fatty Acids
Minimum inhibitory concentration in micrograms/mL for Staphylococcus

| Monocaprin | Monolaurate | Dilaurin | 13 Carbon Mono |
|---|---|---|---|
| 500 | 250 | No inhibition | No Inhibition |

Now reported are in vitro Minimum Inhibitory Concentrations (MIC) for glycerol monolaurate against Staphylococcus aureus MRSA, ATCC 33591, Staphylococcus aureus VISA (Vancomycin intermediate sensitivity) ATCC 700699 and Vancomycin resistant Enterococcus faecalis ATCC 51299 (formerly Streptococcus faecalis VRSF). The results are shown in Table IV. The MIC for glycerol monolaurate against the antibiotic-resistant Staphylococcus strains tested is 62.5 µg/mL. When combined with the other components of the formulation a synergistic effect is seen such that bactericidal activity is still maintained even when the concentration of glycerol monolaurate is reduced to 15 µg/mL.

TABLE IV

Test Results for Glycerol Monolaurate
Final Concentration in micrograms/mL

| Challenge Organism | 250 | 125 | 62.5 | 31.25 | MIC |
|---|---|---|---|---|---|
| S. aureus MRSA | 0 | 0 | 0 | + | 62.5 |
| S. aureus VISA | 0 | 0 | 0 | + | 62.5 |

TABLE IV-continued

Test Results for Glycerol Monolaurate
Final Concentration in micrograms/mL

| Challenge Organism | 250 | 125 | 62.5 | 31.25 | MIC |
|---|---|---|---|---|---|
| Enterococcus faecalis | 0 | 0 | + | + | 125 |

Results expressed as Growth (+) or No Growth (0).
MIC = Minimum Inhibitory Concentration Glycerol monolaurate is a lipophilic surfactant/emulsifier. The exact mode of action for antibacterial activity against gram-positive organisms is unknown but may involve effects on the bacterial cell envelope or cell membrane. Another hypothetical mode of action could be induction of autolysis activity.

Glycerol esters of fatty acids are not irritating to mucous membranes. Glycerol monolaurate is the preferred fatty acid ester. Glycerol monolaurate is available from Lauricidin, Inc. Galena, Ill. A preferred concentration of glycerol monolaurate is 0.01% to 5.0%. A more preferred concentration of glycerol monolaurate is 0.01% to 5.0%. The most preferred concentration of glycerol monolaurate is 0.1% to 5.0%.

Use of Benzoic Acid in Formulation

Benzoic acid is an organic acid which is a naturally occurring derivative of benzene consisting of a carboxyl group attached to a phenyl group. This acid has been found to exhibit antibacterial activity against gram-positive bacteria while also being non-irritating to tissues in the concentrations used in the formulation.

The Minimum Inhibitory Concentration (MIC) for benzoic acid was determined against Staphylococcus aureus MRSA. The results are shown in Table V below. The MIC for benzoic acid against the antibiotic-resistant strain tested is 1250 µg/mL. When combined with the other components of the formulation a synergistic effect is seen such that bactericidal activity is still maintained even when the concentration of benzoic acid is reduced to 312.5 µg/mL.

TABLE V

Challenge organism S. aureus MRSA
Average CFU/mL 8.9 × 10$^6$

| | Benzoic Acid concentration | | | | | |
|---|---|---|---|---|---|---|
| Tube | 10,000 µg/mL | 5,000 µg/mL | 2,500 µg/mL | 1,250 µg/mL | 625 µg/mL | MIC |
| Result | 0 | 0 | 0 | 0 | + | 1250 µg/mL |

Results expressed as Growth (+) or No Growth (0)

Synergism of Formulation Components

It has now been found that, when combined, dodecanol, glycerol monolaurate and benzoic acid exhibit a synergistic antibacterial effect against gram-positive bacteria, specifically MRSA. The MIC for dodecanol was experimentally determined to be about 83 micrograms/mL, the MIC for glycerol monolaurate was experimentally determined to be about 62.5 micrograms/mL, and the MIC for benzoic acid was experimentally determined to be about 1250 micrograms/mL. The MIC results of the component combination are shown in Table VI. When dodecanol was combined with a second component, glycerol monolaurate, the minimum inhibitory concentrations was experimentally determined to be about 40 µg/mL for dodecanol and 30 µg/mL for glycerol monolaurate, thus demonstrating an additive antibacterial effect and that the two components were not inhibited by each other. When a third component, the organic acid benzoic acid, was added to the formulation, the MICs for all three were much lower. As seen in the table below, when the concentration of the dodecanol is 20 µg/mL and the concentration of glycerol monolaurate is 15 µg/mL, the benzoic acid can be decreased from its individual MIC of 1250 µg/mL to 312.5 µg/mL and the formulation still maintains full bactericidal potency. The concentration of each of the components can be reduced to less than one-fourth of the MIC for the components individually while retaining full bactericidal potency against MRSA, thus demonstrating unexpected synergism.

TABLE VI

Synergism of Combination of Dodecanol, Glycerol Monolaurate and Benzoic Acid
Dodecanol (20 µ/mL) and Glycerol Monolaurate (15 µ/mL) concentrations held constant with decreasing concentrations of Benzoic Acid

| Tube | Solution 1 Benzoic Acid 1250 µg/mL | Solution 2 Benzoic Acid 625 µg/mL | Solution 3 Benzoic Acid 312.5 µg/mL | MIC |
|---|---|---|---|---|
| Result | 0 | 0 | 0 | <312.5 µg/ml |

Results expressed as Growth (+) or No Growth (0)

In Vitro Time-Kill Studies for Formulation Comprising Dodecanol and Glycerol Monolaurate Dodecanol and glycerol monolaurate were diluted to 2,000 micrograms/mL and then diluted to the following concentrations: Dodecanol: 100 micrograms/mL and glycerol monolaurate: 250 micrograms/mL. Each challenge organism was confirmed by Gram stain and colony morphology. The sterility controls exhibited no growth. The resistance profile confirmation did not exhibit a zone of growth inhibition when *Staphylococcus aureus* MRSA was exposed to an oxacillin antibiotic disk thus confirming resistance. Log reductions and percent reductions presented in Tables VII and VIII below were calculated using the following equations:

| Enumeration is expressed as colony-forming units (CFU)/mL |
|---|
| Average Initial Controls minus Test Results / Average Initial Count of the Control |
| Multiply × 100 = Percent Reduction |
| Log(Average Initial Counts Control) minus Log Test Results = Log Reduction |

TABLE VII

Initial Counts and Test Results for Glycerol Monolaurate at 250 µg/mL
Initial Count $5.6 \times 10^6$

| | Contact Time | CFU Recovered | % Reduction | Log Reduction |
|---|---|---|---|---|
| *Staphylococcus aureus* MRSA, ATCC 33591 | One Minute | $<5 \times 10^0$ | 100 | 6.75 |

TABLE VII-continued

Initial Counts and Test Results for Glycerol Monolaurate at 250 µg/mL
Initial Count $5.6 \times 10^6$

| | Contact Time | CFU Recovered | % Reduction | Log Reduction |
|---|---|---|---|---|
| *Staphylococcus aureus* VISA, ATCC 700699 | One Minute | $<5 \times 10^0$ | 100 | 7.1 |
| *Enterococcus faecalis* ATCC 51299 | One Minute | $<5 \times 10^0$ | 100 | 7.04 |

Initial Count and Test Results for Glycerol Monolaurate tested at 250 micrograms/mL expressed as Average CFU per mL. Recovered. Percent and Log Reduction.

TABLE VIII

Initial Count and Test Results for Dodecanol at 100 µg/mL
Initial Count $5.6 \times 10^6$

| | Contact Time | CFU Recovered | % Reduction | Log Reduction |
|---|---|---|---|---|
| *Staphylococcus aureus* MRSA, ATCC 33591 | One Minute | $<5 \times 10^0$ | 100 | 6.75 |
| *Staphylococcus aureus* VISA, ATCC 700699 | One Minute | $<5 \times 10^0$ | 100 | 7.18 |
| *Enterococcus faecalis* ATCC 51299 | One Minute | $<5 \times 10^0$ | 100 | 7.04 |

Initial Count and Test Results for Dodecanol tested at 100 micrograms/mL expressed as Average CFU per mL. Recovered. Percent and Log Reduction The log kill achieved in one minute by dodecanol, and glycerol monolaurate is quite significant. It is foreseen that the clinical application of each ingredient could achieve an outstanding log kill when applied to mucous membranes or intact skin to eradicate antibiotic resistant gram-positive organisms. The effectiveness of glycerol monolaurate and dodecanol in achieving a large log kill within a minute has been unknown until now. The time-kill results from previous work would suggest that the compounds would take as long as eight hours to be effective. The log-kill was tested down to a time frame of one minute. An outstanding seven log kill was obtained within one minute as seen in the results above.

There have been reports that dodecanol can be irritating to skin upon repeated exposure, however in the current invention it has been found that the minimum inhibitory concentration of dodecanol (83 µg/mL) is well beneath the threshold where irritation could occur. The concentration of dodecanol is further reduced in the two-component formulation as used since there is an additive effect between the dodecanol and the glycerol monolaurate allowing the amount of dodecanol to be reduced to 40 µg/mL. See Table IX below. Further reduction of the dodecanol can be achieved in the three-component formulation where addition of the benzoic acid leads to a synergistic effect between the dodecanol, glycerol monolaurate and benzoic acid, in which the effective concentration of dodecanol can be further reduced to 20 µg/mL, the concentration of glycerol monolaurate reduced to 15 micrograms/ml and the concentration of benzoic acid reduced to 312.5 micrograms/ml.

TABLE IX

Additive Effect of Dodecanol and Glycerol Monolaurate
S. aureus MRSA - Average CFU/mL = $7.0 \times 10^6$

| Tested Concentration | Result |
|---|---|
| 40 μg/mL Dodecanol | 0 |
| 30 μg/mL Glycerol monolaurate | |
| 20 μg/mL Dodecanol & | + |
| 15 μg/mL Glycerol monolaurate | |
| MIC | 40 μg/mL Dodecanol |
| | 30 μg/mL Glycerol monolaurate |

Expressed as Growth (+) or No Growth (0)
MIC = Minimum Inhibitory Concentration
MIC for Dodecanol = 83 μg/mL and MIC for Glycerol monolaurate = 62.5 μg/mL The nasal formulation of the invention was tested against *S. aureus* MRSA, ATCC 33591. The contact time for the formulation with the bacteria was one minute, after which time, an 8.3 log reduction in bacterial count was observed. The results are presented in Table X below.

TABLE X

Efficacy of Nasal Formulation against MRSA
*Staphylococcus aureus* MRSA, ATCC 33591
Initial Count $1.2 \times 10^9$

| Test Agent | Replicate | Test Recovered (CFU/mL) | Percent reduction | $Log_{10}$ reduction |
|---|---|---|---|---|
| MRSA | 1 | $<5 \times 10^0$ | >99.99 | >8.38 |
| Nasal Formulation | 2 | $<5 \times 10^0$ | >99.99 | >8.38 |

Active ingredients in MRSA Nasal Formulation: dodecanol, glycerol monolaurate, benzoic acid, eucalyptus oil & propylene glycol.

The hand and body wash formulation of the invention was tested against *S. aureus* MRSA, ATCC 33591 and MDR *Klebsiella pneumoniae* ATCC CI-2004. The contact time for the formulation with the bacteria was one minute, after which time, an 8.3 log reduction in bacterial count was observed for *S. aureus* and an almost seven-log reduction was observed for *K. pneumoniae*. The results are presented in Table XI below.

TABLE XI

Efficacy of Hand and Body Wash against Resistant Bacteria

| Test Agent (CFU/mL) | Replicate | Test Recovered | Percent reduction | $Log_{10}$ reduction |
|---|---|---|---|---|
| *Staphylococcus aureus* MRSA, ATCC 33591 Initial Count $1.8 \times 10^9$ | | | | |
| Eucalyptol Hand and Body Wash | 1 | $<5.0 \times 10^0$ | >99.99 | >8.56 |
| | 2 | $<5.0 \times 10^0$ | >99.99 | >8.56 |
| MDR *Klebsiella pneumoniae* ATCC CI 2004 Initial count: $3.9 \times 10^7$ | | | | |
| Eucalyptol Hand and Body Wash | 1 | $<5.0 \times 10^0$ | >99.99 | >6.89 |
| | 2 | $<5.0 \times 10^0$ | >99.99 | >6.89 |

Active ingredients in MRSA Hand & Body Wash: ethyl alcohol, dodecanol, glycerol monolaurate, benzoic acid & eucalyptus oil

EXAMPLES OF SUCCESSFUL TREATMENT OF MRSA LESIONS USING THE NOVEL FORMULATIONS OF THE INVENTION ARE PROVIDED BELOW

Example 1

A male, age 20, was diagnosed with a MRSA abscess approximately 1½ cm in circumference, located above the left eyebrow. He did not use any oral antibiotics or antibiotic ointments prior to applying the formulation ointment comprising dodecanol and glycerol monolaurate directly to the abscess. The subject applied the ointment directly to the wound two times for two days, a total of 4 treatments. The third day after the first application of the ointment, the abscess and any sign of pus or infection had disappeared.

Example 2

A female, age 51, the mother of the patient referenced in Example 1, discovered a small abscess on her right cheek. The abscess and surrounding area was treated with the formulation ointment comprising dodecanol and glycerol monolaurate. All signs of infection were in remission the day following treatment.

Example 3

A male, age 78, was diagnosed with multiple MRSA abscesses on his right index, ring and middle fingers. The patient was under his doctor's care and received several antibiotics, both topical and systemic. After three weeks the patient showed no improvement and his case worsened. The patient was provided with the formulation ointment comprising dodecanol and glycerol monolaurate and instructed to treat his nose as well as to topically treat the abscesses with the formulation ointment. Within a week all the abscesses were dry and free of infection.

Example 4

A female, age 12, was diagnosed with MRSA. The abscess was located on the left side of the patient's posterior. The patient received several types of antibiotics and creams over a period of two and half weeks with no success. A physician drained the abscess 3 times, but the abscess increased in size eventually to 3 centimeters. Upon being treated with the formulation ointment comprising dodecanol and glycerol monolaurate in the nares and directly on the abscess, within four days the abscess decreased in size and was dry and infection free.

Example 5

A male, age 38, the father of the patient referenced in Example 4, spotted a small MRSA abscess on his left thigh. The abscess was treated with the formulation ointment comprising dodecanol and glycerol monolaurate and the ointment was also applied to the nares. The next day the abscess was markedly improved and the infection was remediated.

Example 6

A female, age 6, was diagnosed with a ½ cm MRSA abscess on her right index finger. The patient had been prescribed an antibiotic which after a week had shown no effect on the abscess. The formulation ointment comprising dodecanol and glycerol monolaurate was applied to the patient's wound and two days later, the abscess was remediated.

Example 7

A female, age 21, had been plagued by recurring incidences of MRSA for several years. MRSA lesions were present on her neck and legs. Several of the abscesses were drained and due to the size, stitches were necessary to close the wounds. The treatment of choice was mupirocin which was applied topically and in the nose. Nose cultures were taken and the MRSA was still present in the patient's sinuses. Prior to application of the formulation ointment, she had been treated for MRSA on six different occasions including with oral antibiotics. A pea-sized abscess was treated with the formulation ointment comprising dodecanol and glycerol monolaurate directly in the wound and in the nose and the lesion disappeared within two days.

Example 8

A female, age 29, had an abscess on the lower right side of her left breast. The abscess was about the size of a pea and was identified as MRSA. The patient was unsuccessfully treated with mupirocin. The abscess grew to the dimension of a half dollar coin. The patient began using formulation ointment comprising dodecanol and glycerol monolaurate on the wound and in the nares. On the morning of the third day, the redness and pus had decreased. By the fourth day, the wound was dry and visible signs of infection were gone.

Example 9

A hospitalized male patient had a persistent problem with MRSA contamination at the site of an in-dwelling catheter, a peripherally inserted central line (PICC), which had been non-responsive to treatment. The site was treated using the formulation ointment comprising dodecanol, glycerol monolaurate, and benzoic acid resulting in complete clearing of the MRSA from the site.

Example 10

A child presents with MRSA in the nares. A formulation ointment comprising benzoic acid, glycerol monolaurate and dodecanol is applied to the nares of the patient. The dodecanol component assists in penetrating the crust inside the nose and synergistically acts with the glycerol monolaurate and benzoic acid to reduce or eliminate MRSA organisms resident in the nares. Transfer of MRSA from the nares to the skin is thus prevented, thereby preventing contamination and possible skin lesions.

Example 11

A 12 year old child presents with recurrent impetigo of the left cheek. The lesions were treated with the MRSA ointment three times a day for one week with resolution. The anterior nares were also treated prophylactically twice a day for three days.

Example 12

Patients presenting for surgical procedures can be treated prophylactically with the formulation of the invention including the nasal and perianal ointment plus the alcohol-based hand and body wash formulation. Patients undergoing those procedures which have a high incidence of post-surgical colonization with MRSA, such as hip and knee replacement, cardiovascular surgery and neurological surgery, as well as immunocompromised patients, such as those with diabetes, AIDS or who are undergoing chemotherapy, would especially benefit from such treatment.

Example 13

Skin Wash Compositions

An adjuvant composition comprising one or more aliphatic alcohols having nine to twelve carbons, a fatty acid glycerol ester, most preferably selected from the group consisting of glycerol monolaurate, glycerol monocapric acid, glycerol monocaprylate and mixtures thereof, and an organic acid, preferably selected from the group consisting of benzoic acid or benzoic acid analogs, lactic acid, mandelic acid or malic acid, most preferably benzoic acid or a benzoic acid analog can be added to alcohol-based hand and body washes, liquid hand soap or skin-washes based on iodophoric compounds, for example povidone-iodine, and the like for application to surfaces of the body which may be colonized or contaminated with MRSA. Additional agents that can be employed in the alcohol-based hand and body washes are persistent agents, most preferably selected from zinc pyrithione, chlorhexidine and triclosan.

Example 14

Pre-Surgery Prophylactic Use

Post-operative infections due to MRSA can be catastrophic to patients following orthopedic, cardiovascular or central nervous system procedures. Patients colonized in the anterior nares with MRSA would benefit from the elimination of this organism to prevent the risk of post-operative infection. This could easily be achieved by applying the novel formulation of the invention to the anterior nares prophylactically in the days prior to surgery. In addition, the patient should use the alcohol-based hand and body wash for three consecutive days prior to surgery.

Example 15

Dialysis Centers

Dialysis centers have become major sources of MRSA infection. Patients, patients' family members and/or the healthcare personnel could be treated with the nasal formulation and/or skin wash compositions in order to eliminate the devastating effects of MRSA in patients undergoing dialysis treatment, particularly those with end stage renal disease.

Example 16

Hospitals and Nursing Homes

Hospitals and chronic long-term care facilities, including nursing homes, often have patients who are colonized with HA-MRSA in the anterior nares. These patients can spread the MRSA organism via their hands to their caretakers, and when hospitalized for acute illnesses, these patients may also transfer the organism to other healthcare personnel and their patients. A nasal formulation according to the invention can be applied to patients upon their presentation to the emergency room or to admittance in order to reduce spread of MRSA to others in the facility. Additional treatments may be added as needed.

Example 17

Wound Treatment

The formulations for wound treatment described herein may be applied directly to wounds such as post operative surgical wounds, leg ulcers, pressure ulcers, diabetic ulcers, graft and donor sites, partial thickness burns and/or traumatic wounds. For treatment of wounds an anesthetic ingredient, such as 2% Xylocaine, may be added to assist in pain management.

I claim:

1. A method of treating a patient in need of treatment to reduce or eliminate the concentration of antibiotic-resistant bacteria colonized on said patient, comprising applying a formulation comprising a C9 to C12 aliphatic alcohol and a C10 to C13 fatty acid glycerol ester to a site of bacterial colonization on said patient.

2. The method of claim 1, wherein said aliphatic alcohol is C10 to C12.

3. The method of claim 2, wherein said aliphatic alcohol is C12.

4. The method of claim 1, wherein said fatty acid glycerol ester is a glycerol monoester.

5. The method of claim 4, wherein said glycerol monoester is selected from the group consisting of glycerol monolaurate, glycerol monocaprin, and glycerol monocaprylate.

6. The method of claim 1, wherein said formulation further comprises an organic acid.

7. The method of claim 6, wherein said organic acid is benzoic acid.

8. The method of claim 1, wherein the antibiotic-resistant bacteria are strains of MRSA (methicillin-resistant *Staphylococcus aureus*).

9. A method according to claim 1, wherein said site of bacterial colonization is selected from the group consisting of the nares and intact skin.

10. A method according to claim 1, wherein said site of bacterial colonization is a wound or skin lesion.

11. A method according to claim 1, wherein said formulation further comprises a penetrating agent.

12. The method according to claim 1, wherein said formulation further comprises a botanical oil as an odorant.

13. The method of claim 12, wherein said botanical oil is Eucalyptus Oil.

14. A formulation for application to the human nares for reducing the concentration of antibiotic-resistant bacteria thereon, comprising a C9 to C12 straight chain alkyl alcohols, a C10 to C13 fatty acid glycerol ester, a penetrating agent, and a carrier ointment.

15. The formulation according to claim 14, wherein said alcohol is C12 dodecanol.

16. The formulation of claim 15, wherein the fatty acid glycerol ester is selected from glycerol monocapric acid, glycerol monocaprylate, and glycerol monolaurate.

17. A method according to claim 9 for rapidly eliminating antibiotic-resistant bacteria from the nares of a human patient, comprising topical application of said formulation to said nares, wherein said aliphatic alcohol is dodecanol in an amount of 10% or less.

18. The method of claim 17, wherein said fatty acid glycerol ester is glycerol monolaurate.

19. The method of claim 17, further comprising topical application to said nares for at least about one minute, whereby a greater than seven log kill of antibiotic resistant bacteria occurs.

20. A formulation to reduce or eliminate gram positive bacteria, comprising a C9 to C12 alcohol and a fatty acid ester selected from glycerol monocapric acid, glycerol monocaprylate, and glycerol monolaurate.

21. The formulation of claim 20, further comprising an organic acid.

22. The formulation of claim 20, wherein said organic acid is benzoic acid.

23. The formulation of claim 20, wherein the topical formulation comprises an iodophore.

24. The formulation of claim 20, further comprising a persistent agent selected from the group consisting of zinc pyrithione, chlorhexidine and triclosan.

25. The formulation of claim 20, further comprising a C2 to C3 alcohol.

26. The formulation of claim 20 adapted for use as an adjuvant for enhancing the effectiveness of a second topical formulation.

27. The formulation of claim 25 adapted for use as a hand and body wash.

* * * * *